United States Patent [19]

Kondo et al.

[11] Patent Number: 4,834,820
[45] Date of Patent: May 30, 1989

[54] METHOD FOR PRODUCING TAPE FOR PUTTING ON DISPOSABLE DIAPER

[75] Inventors: Takahisa Kondo, Saitama; Masami Sekimoto, Hyogo, both of Japan

[73] Assignee: Star Rubber Kogyo Kabushiki Kaisha, Kobe, Japan

[21] Appl. No.: 221,278

[22] Filed: Jul. 19, 1988

Related U.S. Application Data

[62] Division of Ser. No. 96,044, Sep. 11, 1989.

[30] Foreign Application Priority Data

Sep. 24, 1986 [JP] Japan .......................... 61-145079[U]

[51] Int. Cl.⁴ ...................... B32B 31/00; B32B 31/26; A61F 13/16; B65D 65/28
[52] U.S. Cl. ................................. 156/73.3; 156/268; 156/289; 156/307.7; 427/372.2; 428/43; 604/390
[58] Field of Search ................. 604/389, 390; 428/43, 428/202, 351, 352; 427/372.2, 385.5, 397.7, 391, 393.5; 156/73.3, 244.15, 268, 269, 289, 307.7, 338

[56] References Cited

U.S. PATENT DOCUMENTS

| | | | |
|---|---|---|---|
| 4,177,812 | 12/1979 | Brown et al. | 604/390 |
| 4,360,398 | 11/1982 | Sabee | 156/268 |
| 4,389,212 | 6/1983 | Tritsch | 604/389 |
| 4,452,657 | 6/1984 | Hamm | 156/307.7 |
| 4,478,887 | 10/1984 | Sommer et al. | 156/307.7 |
| 4,643,729 | 2/1987 | Laplanche | 604/389 |
| 4,786,349 | 11/1988 | Ales et al. | 156/289 |

Primary Examiner—Michael W. Ball
Assistant Examiner—Louis Falasco
Attorney, Agent, or Firm—Roger J. French

[57] ABSTRACT

A method for producing a tape for putting on a disposable diaper which comprises an elastic sheet (1) and a non-flexible bonded retaining sheet (2). The retaining sheet (2) is bonded at least in part to the elastic sheet (1) and provided with at least one cut-off groove (4).

4 Claims, 2 Drawing Sheets

METHOD FOR PRODUCING TAPE FOR PUTTING ON DISPOSABLE DIAPER

This is a divisional of co-pending application Ser. No. 096,044, filed on Sept. 11, 1987.

FIELD OF INVENTION AND RELATED ART STATEMENT

This invention relates to a flexible tape for putting on a disposable diaper.

The tape employed heretofore for putting a disposable diaper on the baby carries an adhesive at one end thereof for attaching it to the side closure part of the disposable diaper. In putting the paper diaper on the baby, members constituting said closure part are pulled toward each other according to the girth of the baby and joined together with the aid of said adhesive in overlapped condition.

However, with this conventional tape, it happens frequently that said members cannot be pulled up toward each other to the optimum extent and particularly because the suckling baby is very active, it is necessary to peel off the tape and re-affix it several times. If the disposable diaper put on is ill-fitting even a little, it is so binding that it interferes with the abdominal respiration of the baby. Moreover, it is troublesome to peel off the tape in order to check for urination or stool.

OBJECT AND SUMMARY OF THE INVENTION

In view of the above problems, this invention is intended to provide a disposable-diaper tape which can be put on easily in one operation, is flexible and does not interfere with the abdominal respiration of the baby after wearing and eliminates the need for peeling off the tape for checking for urination and stool.

The disposable-diaper tape of this invention is characterized in that it comprises an elastic sheet and a non-flexible retaining sheet which is at least partly bonded to said elastic sheet, with said retaining sheet being provided with at least one cut-off groove.

BRIEF DESCRIPTION OF THE DRAWINGS

Embodiments of the present invention are described below with reference to the accompanying drawings in which.

DETAILED DESCRIPTION OF PREFERRED EMBODIMENTS

Figure 1:
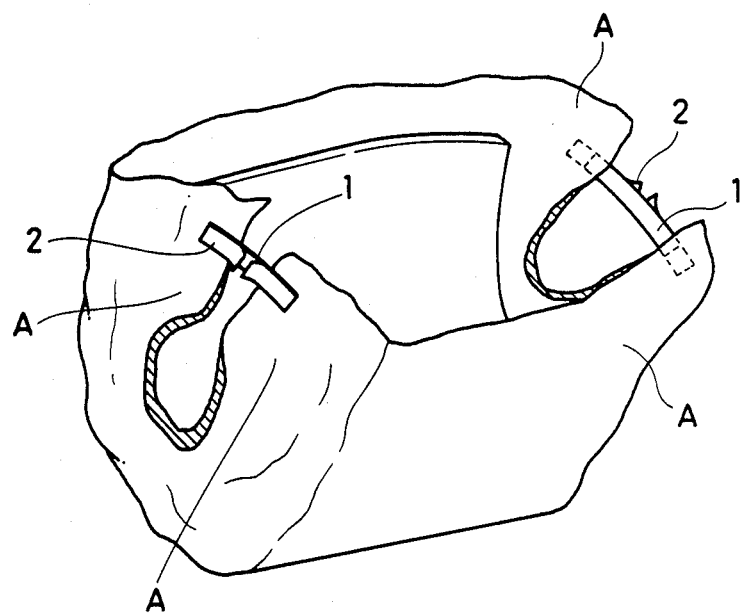
FIG. 1 is a perspective view showing an example of use of the first embodiment.
Figure 2:
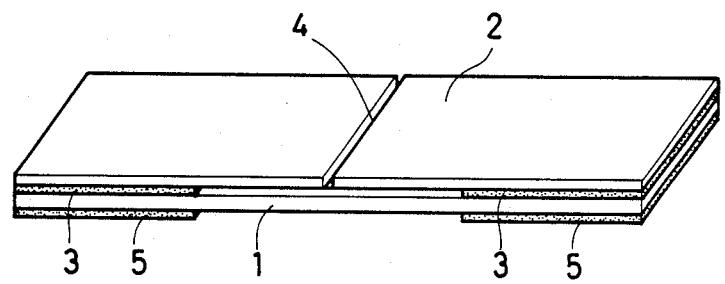
FIG. 2 is a perspective view of said embodiment of this invention.

Referring to FIGS. 1 and 2, the disposable-diaper tape according to the first embodiment of this invention comprises an elastic sheet 1 and a non-flexible retaining sheet 2 and is disposed between members A, A of the side closure part of a disposable diaper.

The elastic sheet 1 is fabricated, for example, by cutting a rubber sheet into a tape form. A polyurethane film or a polyurethane foam can likewise be employed for this purpose.

Figure 3:
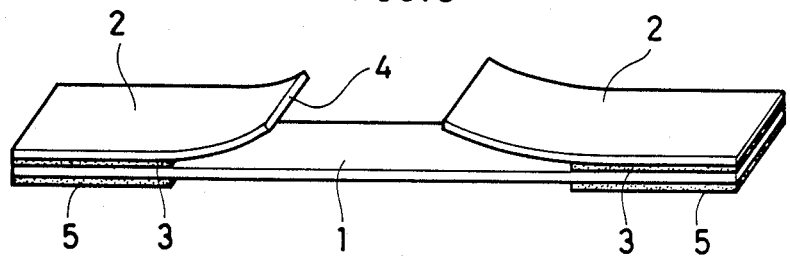
FIG. 3 is a perspective view showing the condition thereof after tearing-off the retaining sheet.

The retaining sheet 2 is made of, for example, OPP (oriented polypropylene) film, other plastic film, non-woven fabric, or fibrous woven material. As clearly shown in FIGS. 2 and 3, the retaining sheet 2 is bonded to the upper side of the elastic sheet 1 at 3, leaving a portion thereof unbonded. In the center of this unbonded portion, there is formed a cut-off groove 4 extending perpendicularly with respect to the longitudinal direction of the sheet.

The elastic sheet 1 is bonded to the paper diaper with an adhesive 5.

A typical method for manufacture of the disposable diaper tape according to this invention will be described below, taking as an example the use of a rubber sheet as said elastic sheet 1 and an OPP film as said retaining sheet 2. At the calendering stage in the rubber sheet manufacturing line, an OPP film is superimposed on the rubber sheet and the assembly is cured in a curing oven. After curing, the sheet is cut to a predetermined width and, at the same time, an incision is made in the center of the OPP film with a cutter or by high-frequency cutting to form a cut-off groove 4, while both end portions are thermally bonded by the high frequency method. An adhesive agent is applied to the undersides of both end portions of the cut rubber sheet while a silicone dope as a releasing agent is applied to the upper surface of the OPP-film and the assembly is taken up to provide a finished product.

The disposable-diaper tape of this invention is used in the following manner.

The retaining sheet 2 is manually ripped apart along the cut-off groove 4, whereupon the center of the elastic sheet 1 held in fixed length by said retaining sheet 2 is made flexible so that the side closure members A and A are free to be opened or closed with an appropriate force.

After the product tape of this invention is attached to the side closure portion of the disposable diaper, the retaining tape is ripped apart along the cut-off groove 4 whereupon the side closure portions of the disposable diaper are made free to be opened and closed. Thus, since there is a reasonable room for stretching even if the diaper is put on without much attention to the baby's girth, it can be easily put on in one operation and the disposable diaper is free to expand and shrink after wearing. Therefore, there is no compressive influence on the abdominal respiration of the baby and one can check for urination or stool simply by opening the disposable diaper freely by hand without peeling off the tape.

Figure 4:
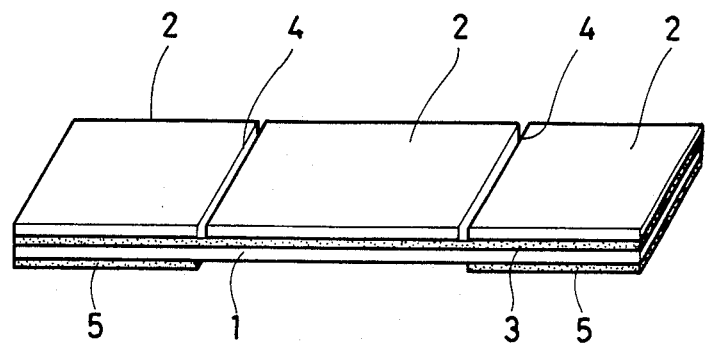
FIG. 4 is a perspective view of a second embodiment.
Figure 5:
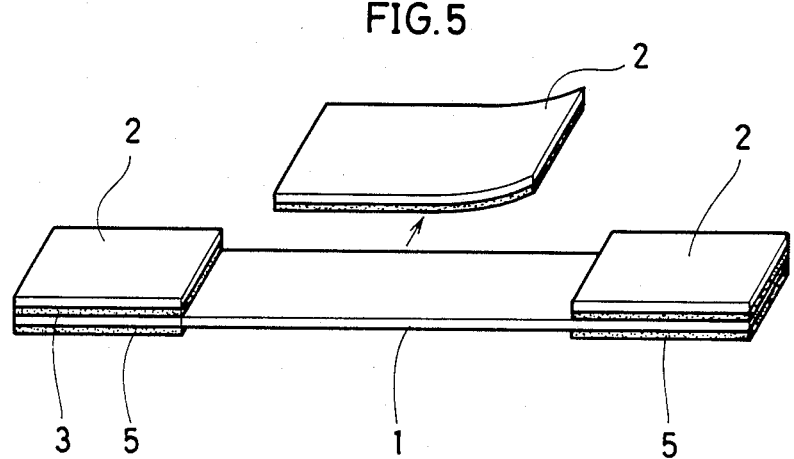
FIG. 5 is a perspective view showing the condition thereof after tearing-off of the retaining sheet.

The disposable-diaper tape shown in FIGS. 4 and 5 is a second embodiment of this invention. The like symbols designate the like parts. The only difference from the first embodiment is that the retaining sheet 2 is provided with two cut-off grooves, instead of one groove, near ends of the central portion. In use, this central portion of the retaining sheet 2 is removed. In this construction, unlike in the first embodiment, there is the advantage that the tape ends left behind after riping-apart will not flap around the side closure portions of the disposable diaper.

The above is a description of some embodiments of this invention and the terminology used is only intended to explain the invention and should not be construed to be limitative of the invention. Many changes and modifications can be made by those skilled in the art without departing from the scope of the accompanying claims.

We claim:

1. A method of producing a tape for putting on a disposable diaper, said tape having a rubber sheet and a non-flexible retaining sheet which is bonded, at least in part, to said rubber sheet and is provided with at least one cut-off groove, comprising the steps of:
   (a) superimposing the retaining sheet on a raw rubber sheet at a calendering stage in the rubber sheet manufacturing line,
   (b) curing the assembly in a curing oven,
   (c) cutting the sheet to a predetermined width and, at the same time, making at least one incision in said retaining sheet with a cutter or by high-frequency cutting to form the cut-off groove for each tape,
   (d) applying an adhesive agent to underside portions of the rubber sheet, and
   (e) applying a silicone dope as a releasing agent to the upper surface of the retaining sheet.

2. A method according to claim 1, wherein two incisions are made to form two cut-off grooves in each tape.

3. A method according to claim 1, wherein only one incision is made to form one cut-off groove in each tape.

4. A method according to claim 1, wherein said non-flexible retaining sheet is made of any one of a group of materials comprising oriented polypropylene (OPP) film, other plastic film, nonwoven fabric material and woven textile material.

* * * * *